United States Patent [19]
Heuscher et al.

[11] Patent Number: 5,485,493
[45] Date of Patent: Jan. 16, 1996

[54] MULTIPLE DETECTOR RING SPIRAL SCANNER WITH RELATIVELY ADJUSTABLE HELICAL PATHS

[75] Inventors: Dominic J. Heuscher, Aurora; Walter W. Lindstrom, Shaker Heights; Heang K. Tuy, Chesterland, all of Ohio

[73] Assignee: Picker International, Inc., Highland Hts., Ohio

[21] Appl. No.: 179,608

[22] Filed: Jan. 10, 1994

Related U.S. Application Data

[63] Continuation-in-part of Ser. No. 139,318, Oct. 19, 1993, Pat. No. 5,396,418, which is a continuation-in-part of Ser. No. 943,411, Sep. 9, 1992, abandoned, and a continuation-in-part of Ser. No. 567,300, Aug. 14, 1990, Pat. No. 5,262,946, which is a continuation-in-part of Ser. No. 260,403, Oct. 20, 1988, Pat. No. 4,965,726, and a continuation-in-part of Ser. No. 438,687, Nov. 17, 1989, Pat. No. 5,276,614.

[51] Int. Cl.$^6$ ................................................ G06F 159/00
[52] U.S. Cl. ............................... 378/686; 378/4; 378/16; 378/151; 378/153; 378/901
[58] Field of Search ........................ 364/413.14, 413.15, 364/413.16, 413.17; 378/4, 9, 14, 15, 23, 92, 145, 146, 147, 150, 19, 7, 153, 17, 143, 43, 16, 901, 151; 250/385.1, 370.09

[56] References Cited

U.S. PATENT DOCUMENTS

| | | | |
|---|---|---|---|
| 4,066,901 | 1/1978 | Seppi et al. | 378/4 |
| 4,075,492 | 2/1978 | Boyd et al. | 378/7 |
| 4,200,799 | 4/1980 | Saito | 378/13 |
| 4,303,863 | 12/1981 | Racz et al. | 250/385.1 |
| 4,426,721 | 1/1984 | Wang | 250/370.09 |
| 4,442,489 | 4/1984 | Wagner | 364/423.15 |
| 4,672,651 | 6/1987 | Horiba et al. | 378/62 |
| 4,789,929 | 12/1988 | Nishimura et al. | 364/413.15 |
| 4,920,552 | 4/1990 | Hermens | 378/153 |
| 4,991,189 | 2/1991 | Boomgaarden et al. | 378/4 |

(List continued on next page.)

FOREIGN PATENT DOCUMENTS

| | | |
|---|---|---|
| 383232A3 | 8/1990 | European Pat. Off. . |
| 426464A3 | 5/1991 | European Pat. Off. . |
| 471455A3 | 2/1992 | European Pat. Off. . |
| 464645A1 | 8/1992 | European Pat. Off. . |
| 2679435A1 | 1/1993 | France . |
| 2732073A1 | 1/1978 | Germany . |
| 4228082C1 | 9/1993 | Germany . |

OTHER PUBLICATIONS

"Physical Performance Characteristics of Spiral CT Scanning", Kalender Med. Phys. 18 (5), Sep./Oct. 1991, pp. 910–915.

"Power–Injected CT Contrast Opacifies Vascular Spaces", Lane, Diagnostic Imaging, Nov. 1988.

"World's Fastest CT. From Zero to 40 in 75 Seconds," Picker Advertising Brochure.

"Spiral Volumetric CT with Single–Breath–Hold Technique, Continuous Transport, and Continuous Scanner Rotation", Kalender, et al. Radiology 1990; 176: 181–183.

*Primary Examiner*—Gail O. Hayes
*Assistant Examiner*—Joseph Thomas
*Attorney, Agent, or Firm*—Fay, Sharpe, Beall, Fagan, Minnich & McKee

[57] ABSTRACT

A CT scanner (10) has an x-ray source (12) which transmits a plurality (N) of x-ray fans across an examination region (14) to a plurality of rings of radiation detectors (28). An adjustable septum (80) adjusts a gap between the fan beams and outer collimators (82) adjust the width of the fan beams such that the effective spacing and width are adjusted. The x-ray source rotates around the examination region as a subject support (32) moves longitudinally through the examination region such that the x-ray fans move along interleaved spiral trajectories. Radiation attenuation data from each of the x-ray fans is combined and reconstructed into a plurality of images along parallel slices orthogonal to the longitudinal axis. The spacing between the x-ray beams is adjusted relative to the effective pitch of the spirals such that the leading edges of the x-ray fans intersect a common transverse plane at 180°/N angular intervals around the longitudinal axis.

24 Claims, 7 Drawing Sheets

U.S. PATENT DOCUMENTS

| | | | |
|---|---|---|---|
| 5,008,822 | 4/1991 | Brunnet et al. | 364/413.21 |
| 5,073,911 | 12/1991 | Ozaki et al. | 378/17 |
| 5,090,037 | 2/1992 | Toth et al. | 378/4 |
| 5,222,114 | 6/1993 | Kamata et al. | 378/143 |
| 5,245,648 | 9/1993 | Kinney et al. | 378/43 |
| 5,268,955 | 12/1993 | Burke et al. | 378/135 |
| 5,365,566 | 11/1994 | Mass | 378/150 |

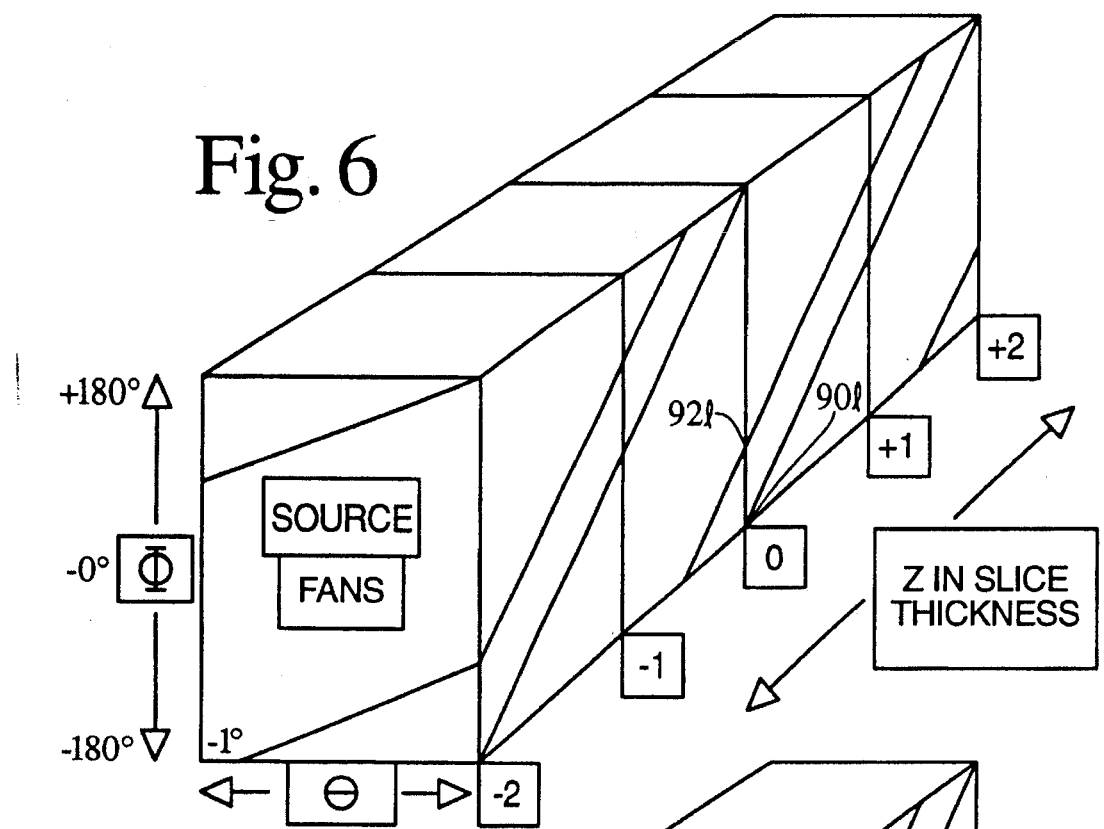

MULTIPLE DETECTOR RING SPIRAL SCANNER WITH RELATIVELY ADJUSTABLE HELICAL PATHS

This application is a continuation-in-part of U.S. application Ser. No. 08/139,318, filed Oct. 19, 1993, now U.S. Pat. No. 5,396,418, which application, in turn, is a continuation-in-part of U.S. application Ser. No. 07/943,411, filed Sep. 9, 1992 (now abandoned) and U.S. application Ser. No. 07/567,300, filed Aug. 14, 1990, now U.S. Pat. No. 5,262,946, which is a continuation-in-part of U.S. application Ser. No. 07/260,403, filed Oct. 20, 1988, now U.S. Pat. No. 4,965,726 and a continuation-in-part of U.S. application Ser. No. 07/438,687, filed Nov. 17, 1989, now U.S. Pat. No. 5,276,614.

BACKGROUND OF THE INVENTION

The present invention relates to the art of diagnostic imaging. It finds particular application in conjunction with spiral volume imaging with CT scanners and will be described with particular reference thereto. However, it is to be appreciated that the invention will also find application in conjunction with other types of volume imaging of human patients for medical diagnostic purposes, of manufactured articles to detect internal structures or flaws, and the like.

In conventional spiral or helical scanning, an x-ray tube rotates continuously as the subject support table moves at a constant, linear velocity. In this manner, the collected data effectively represents a helical path of constant pitch through the subject. In some spiral scanners, a second spiral scan is collected in either the same direction after retrace or in the opposite direction during retrace. Retrace is the return of the subject support to the initial starting position.

Rather than collecting the second helical path of data after the retrace, the data along the second or larger plurality of helical paths can be collected concurrently with the first helix. Multiple rings of detectors, as illustrated in the parent applications hereto, enable data to be collected along two or more helical paths concurrently.

Commonly, the image data are stored and handled as a series of parallel planar images or slices transverse to the longitudinal axis of the subject. More specifically, the collection of planar slices is typically treated as a three dimensional rectangular matrix of image information. That is, the data collected along the helical paths is reconstructed into a series of planar slices.

One technique for reconstructing image slices from spiral data is to use interpolation or weighting to convert the spiral data to planar data. For example, for each plane, the corresponding rays in the two closest spirals to either side of the plane are interpolated to generate one of the rays of the planar data set. This same interpolating procedure is repeated for each ray of a complete data set, e.g. a 180° plus fan beam data set. This data can then be reconstructed into a planar image representation using conventional reconstruction techniques.

In order to optimize the resolution of the reconstructed data and resultant images, it would be advantageous to minimize the pitch of the helixes, i.e. minimize longitudinal movement of the subject support per revolution. However, the pitch is often constrained by the selected size of the imaged volume and the selected duration within which the data is to be collected. For human subjects, particularly in areas where organs are moving, the volume scan must be conducted sufficiently quickly that image degradation from organ movement is minimized. Once the image scan time and the size of the volume are fixed, the pitch is constrained.

Another factor for optimizing the resolution is the spacing between the adjacent detector rings. At first blush, it might appear that minimizing the detector spacing would optimize resolution. The inventors herein have determined that minimizing the detector spacing in most cases does not optimize the resolution.

Previously, dual slice spiral CT scanning was considered to aid only in x-ray photon utilization. Using two interleaved spirals does not necessarily generate higher resolution data. Much of the data is redundant or partially redundant, i.e. taken along time displaced fully or partially overlapping rays. The redundant rays are combined to double the x-ray photon utilization, but the redundant rays do not in general double the sampling.

The present application contemplates a new and improved multiple helix scanning technique which overcomes the above-referenced problems and others.

SUMMARY OF THE INVENTION

In accordance with the present invention, a method of CT scanning along a plurality of paths of common pitch is provided. The trajectory or longitudinal offset of at least one of the helical paths is adjustable relative to the other(s).

In accordance with another aspect of the present invention, a CT scanner is provided which includes an x-ray source, multiple parallel detector rings, and a means for moving a subject support and the x-ray source/detector rings longitudinally relative to each other. A means is provided for selectively adjusting an effective center-to-center spacing of the detector rings.

In accordance with a more limited aspect of the present invention, a means for adjusting the effective spacing of the detector rings includes an adjustable septum and adjustable outer collimator blades.

One advantage of the present invention is that it provides greater x-ray photon utilization.

Another advantage of the present invention is that it allows faster scan times.

Another advantage of the present invention is that it permits greater coverage.

Another advantage of the present invention resides in the flexibility to select a desired effective pitch factor (with gap and slice thickness) to optimize image quality for a given speed and coverage.

Still further advantages of the present invention will become apparent to those of ordinary skill in the art upon reading and understanding the following detailed description of the preferred embodiments.

BRIEF DESCRIPTION OF THE DRAWINGS

The invention may take form in various components and arrangements of components, and in various steps and arrangements of steps. The drawings are only for purposes of illustrating a preferred embodiment and are not to be construed as limiting the invention.

FIG. 6 is a graphic illustration of the spiral trajectory for a pitch factor of 2 with half gap rings;

FIG. 7 illustrates the pitch factor equal to 2 and half gap detector ring spacing with the ray direction redundancy removed;

DETAILED DESCRIPTION OF THE PREFERRED EMBODIMENTS

Figure 1:
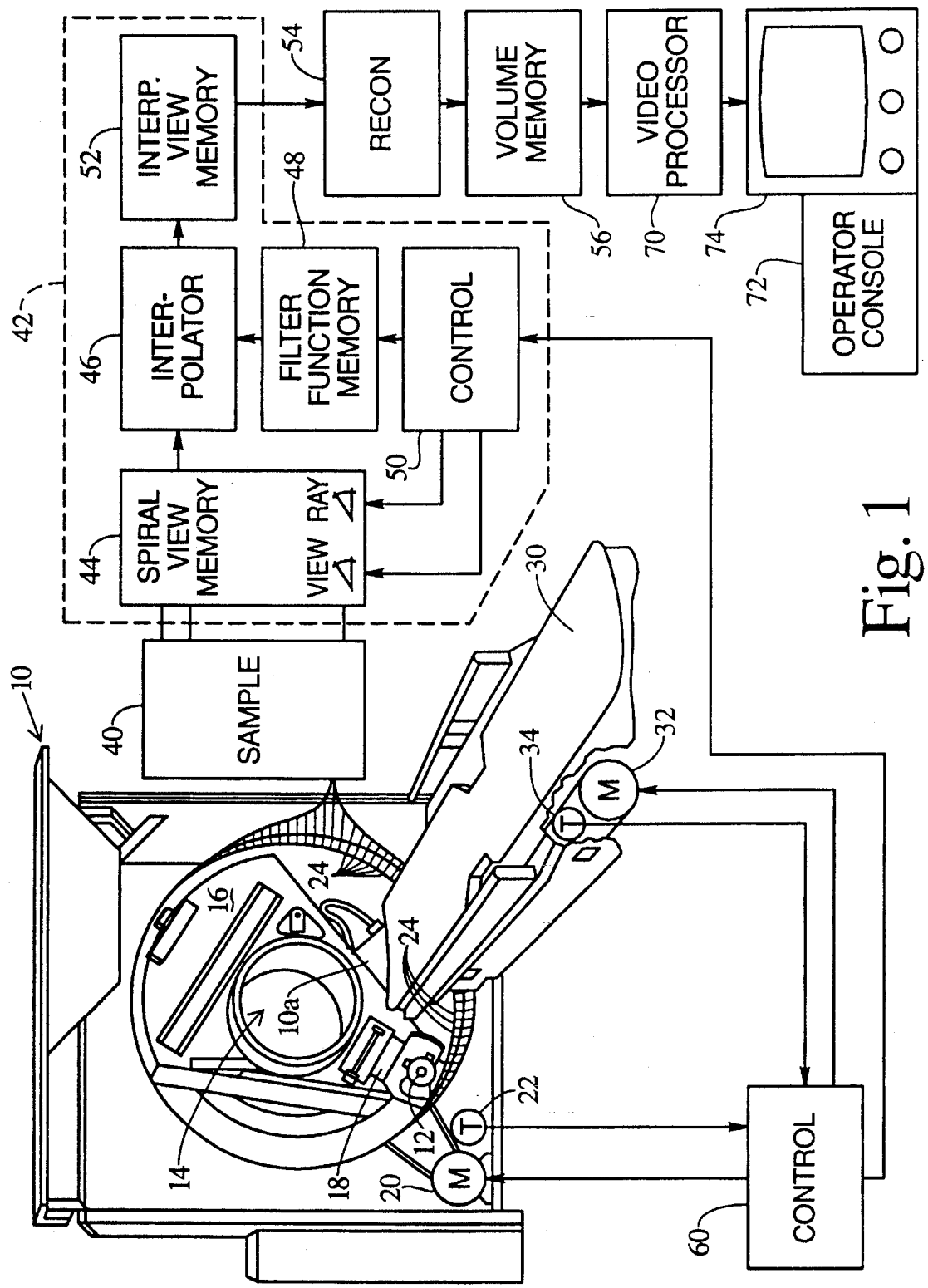
FIG. 1 is a diagrammatic illustration of a CT scanner in accordance with the present invention.

With reference to FIG. 1, a CT scanner 10 includes a radiation source 12, such as an x-ray tube, for projecting a fan beam of radiation through an examination region or scan circle 14. The x-ray tube is mounted on a rotatable gantry 16 to rotate the fan beam of radiation around the examination region. A collimator and shutter means 18 collimates the radiation to a pair or more narrow planar beams and selectively gates the beam on and off. The beams may be also gated on and off electronically at the x-ray tube. A motor 20 provides motive power for rotating the gantry 16 continuously around the examination region. A rotational position encoder 22 is connected with the motor and the gantry to measure the rotational position of the gantry. In the illustrated fourth generation CT scanner, a ring of radiation detectors 24 are mounted peripherally around the examination region.

In a source fan geometry, an arc of detectors which span the radiation emanating from the source are sampled concurrently at short time intervals as the radiation source 12 rotates in back of the examination region 14 to generate views or fan data sets. The path between the x-ray source and each of the detectors is denoted as a "ray". The apex of each fan has an absolute angular orientation Φ within the orientation of the slice. Within each fan, the relative angle of each ray is denoted by the angle θ. The ray angle θ determines a radius r of each ray from a scan center, i.e. a centerline of the scan. As the x-ray source rotates around the subject, the right-most ray of the source fans, for example, will rotate through 360°. However, because radiation attenuation is direction independent, in each 360° of rotation, each ray will be collected twice.

A patient couch 30 supports a subject, particularly a human patient, in a reclined position. A means, such as a motor 32, advances the patient supporting surface of the couch through the examination region at a selectable velocity. An encoder 34 is connected with the motor 32, the moveable patient supporting portion 30, and the drive mechanism therebetween for monitoring the actual position of the patient supporting surface as it moves the patient through the scan circle 14.

A sampling means 40 samples the fan views or data sets corresponding to each angular position around the examination region 14 for each of a multiplicity of helical scans.

A view processor 42 converts the spiral sampled views of each helical scan into data sets ready for reconstruction into a plurality of parallel image planes sampled over a limited time range. The view processor includes a view memory 44 in which the stored view data is addressable by a combination of the scan number (or time), rotation number, view angle, and ray angle within the view. The view processor 42 further includes a filter or interpolation means 46 for interpolating the data of each helical scan in the spiral view memory 44 into parallel slice data. The interpolation means 46 operates on a plurality of views of corresponding view angle with a filter or interpolation function supplied by a filter function memory 48.

The filter function memory means 48 stores a plurality of filter or interpolation functions such as a linear weighting function, a cubic weighting function or other appropriate helical weighting function.

A control means 50 indexes the view angle to each of the view angles in a complete helical scan, e.g. the views disposed at regular increments around the examination region. Each view is stored and interpolated view memory means 52 until the interpolated views corresponding to each interpolated slice are generated. An image reconstruction means 54 uses a conventional filtered backprojection or other reconstruction algorithm to reconstruct each of a plurality of data slices and store the resultant image slices in a three-dimensional volume image memory 56. A control means 60 controls the motor 20 such that the x-ray source is rotated at a constant rate, e.g. about 1 second per revolution. The control means 60 also controls the motor 32 which control movement of the subject table 30. To cover a volume which is 15 cm in the axial or z-direction in 10 seconds, the patient table is moved at about 15 mm per second. The control 60 also gates the x-ray tube off or closes the shutter 18 such that the patient is not irradiated during return or retrace periods.

An image and video processor 70 is controlled by a console 72 to select two-dimensional images from the three-dimensional image data set for display. The processor means selects various two-dimensional image representations such as planar slices through the volume at various angles and at various times, series of images through the same slice showing evolution over time, projection images, segmented or cut-away images, or the like. The processor can also superimpose data from two or more images, such as superimposing a contrast agent image and a surrounding tissue image. The video processor converts the selected image representation(s) into appropriate format for display on a video monitor 74. Optionally, additional image processing means, image memory storage and archiving means, and the like may be provided.

Figure 2:
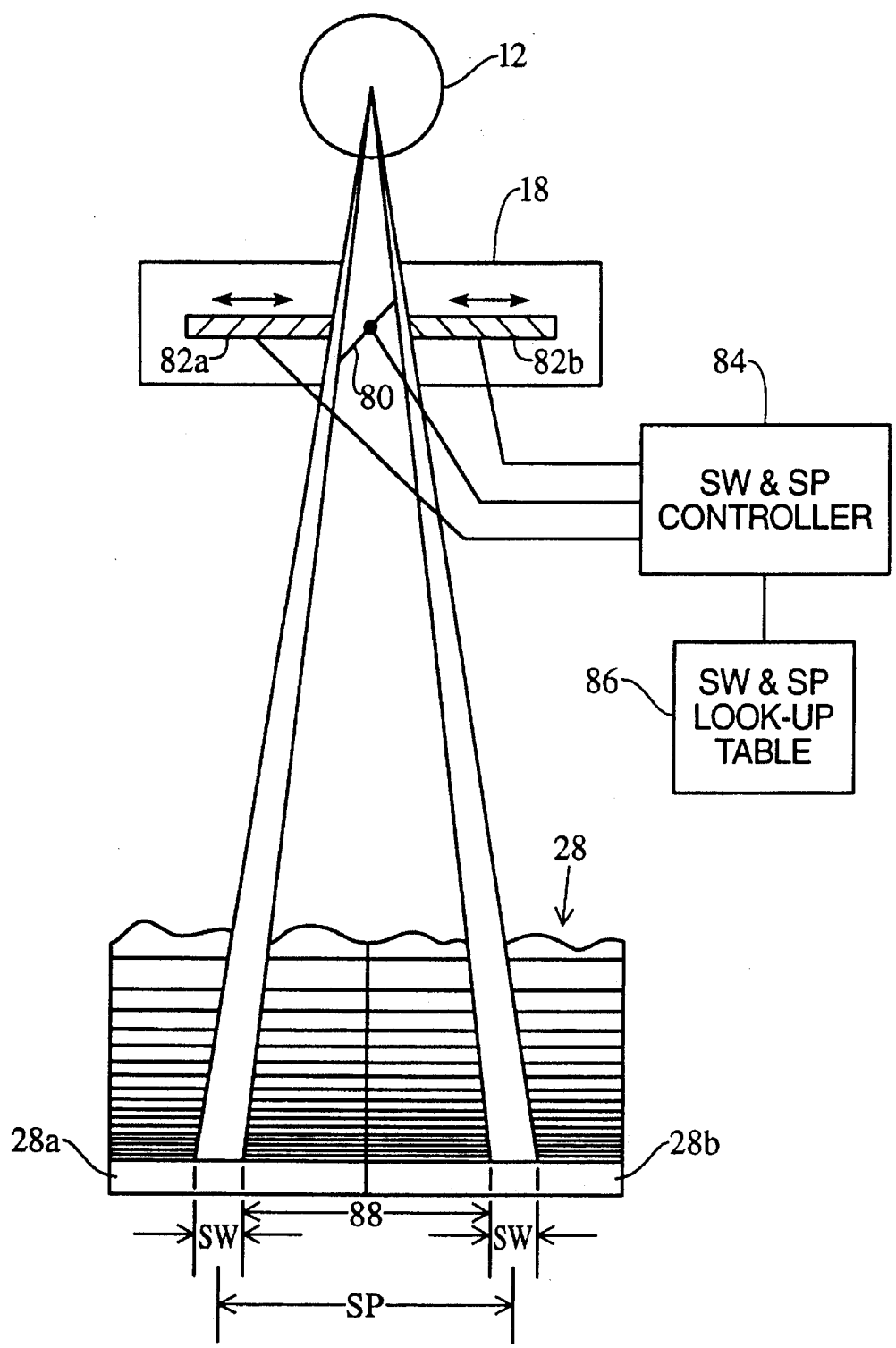
FIG. 2 is a side view in partial section of a portion of an x-ray source, segmented detector array, adjustable septum, and adjustable outer collimators for adjusting the effective slice width and the effective detector ring spacing.

With particular reference to FIG. 2, a plurality of detector rings are provided, such as detector rings 28a and 28b. The collimator 18 includes an adjustable septum 80. The septum adjusts the width of the x-ray beams, hence an effective slice width SW. Adjustable outer collimator blades 82a, 82b located either in the collimator or on the x-ray detector array adjust the width of the beams. A collimation control 84 adjusts the septum 80 and the outer collimators 82a, 82b in accordance with settings from a look-up table 86 to adjust both the slice width SW and an effective detector spacing SP. The look-up table is preprogrammed in accordance with the tables and formulas described below.

A gap 88 between fans is equal to the distance between the detector spacing and the slice width, i.e. SP–SW, for a two-slice system. A gap ratio, i.e. the gap divided by the slice width, can be described mathematically as: (SP–SW)/SW.

Figures 3, 4:
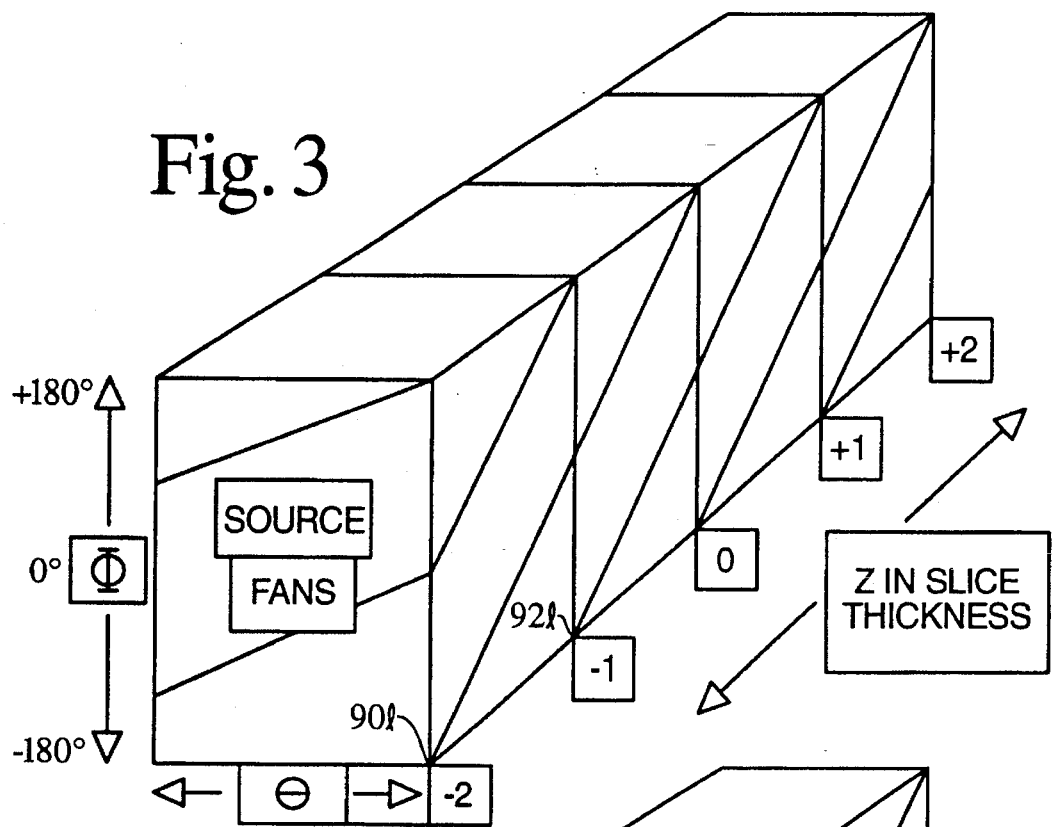
FIG. 3 illustrates a spiral trajectory for a pitch factor of 2 with abutting rings.
FIG. 4 illustrates the spiral trajectory of FIG. 3 with the ray direction redundancy removed.

As illustrated in FIG. 3, if the septum 80 is removed such that the two helices abut, there is only one sample per slice width, for any ray direction ($\theta,\Phi$). This is shown more clearly in FIG. 4 in which the redundancy is removed.

Figure 5:
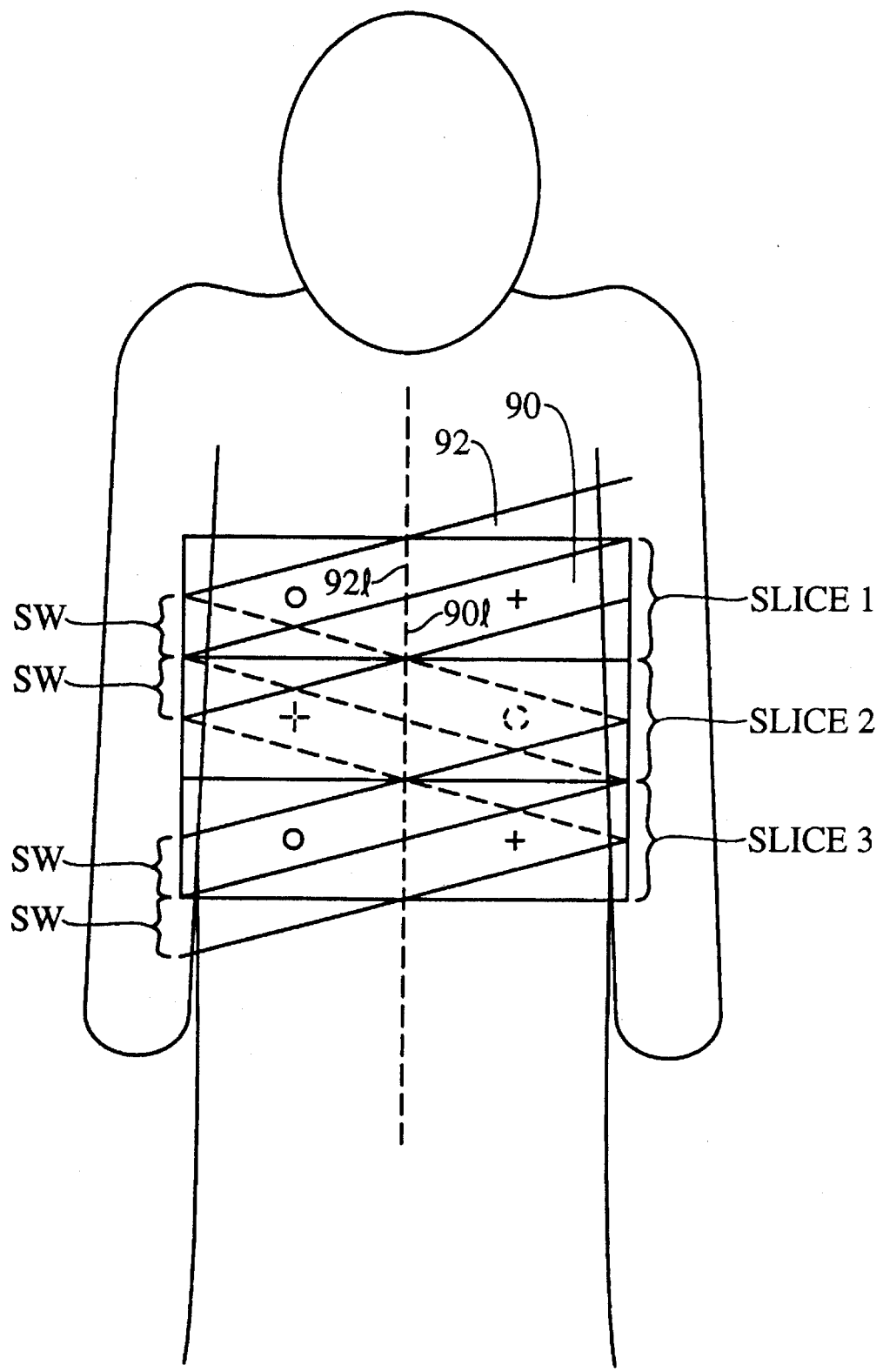
FIG. 5 is a top view of a patient illustrating a spiral trajectory with a pitch factor of 2 and half ring gaps.

With reference to FIGS. 5 and 6, the pitch is twice the slice width, i.e. a pitch factor of 2. To get an effective pitch factor of 1, for good image quality, the gap between the slices is set to exactly ½ the slice width. In this manner, as will be obvious from FIG. 7 with the redundancy removed, setting the gap at ½ the slice width causes an equal 2 samples per slice width to be generated for any ray direction ($\theta,\Phi$). By using a completely adjustable gap between the x-ray fans, a complete freedom in the selection of the spiral pitch and the "effective pitch factor" can be improved by a factor of 2 relative to a single detector ring of the same pitch.

As illustrated in FIG. 5, the trajectory of the two helices should be such that a central ray of the fan of a leading helix 90 crosses a central plane of each slice 90° ahead of a central ray of the corresponding fan of a trailing helix 92. Stated another way with reference to FIGS. 6 and 7, in a two helix system, the trajectory of the second helix should be selected such that a leading edge 901 of one of the fan beams crosses an arbitrary plane perpendicular to the z-axis at the same angle as a leading edge 921 of the other fan. More specifically, the second helix should trail the leading helix by 90° in a two-ring system, 60° in a three-ring system, or 180°/N in a N-ring system.

Figure 8:
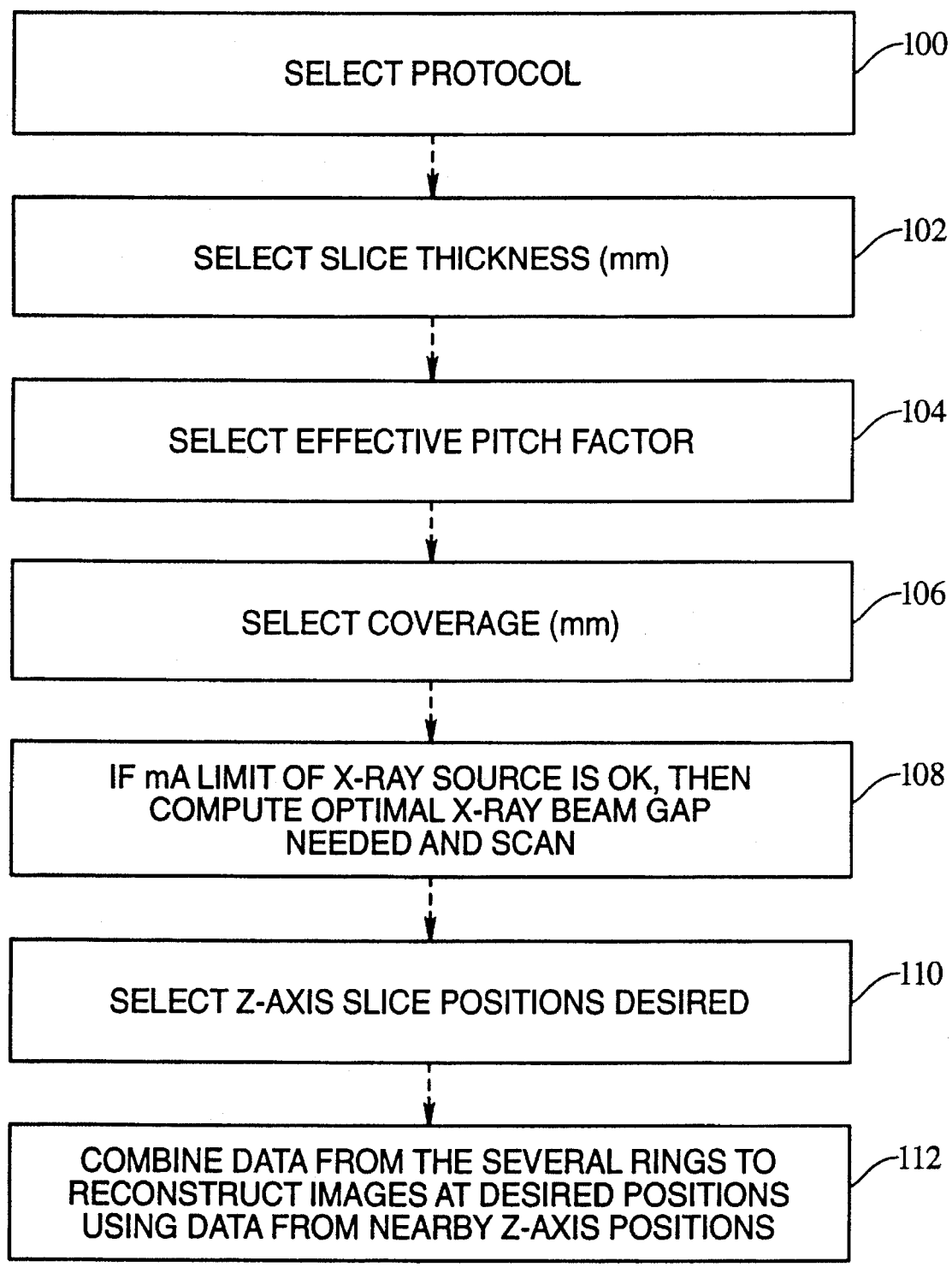
FIG. 8 is a flow diagram for multiple spiral ring scanning.

With reference to FIG. 8, the method for selecting the gaps starts with a step or means 100 for selecting a CT protocol. This includes responding to operator selections of a console of x-ray parameters such as intensity, duration, filtration, and the like by generating corresponding electronic selection signals. Next, a step or means 102 selects the desired z-axis x-ray resolution, i.e. the slice thickness in millimeters and an effective pitch factor. The slice thickness and effective pitch factors determine the pitch, preferably in millimeters. The pitch is the distance which the subject is advanced relative to the x-ray fan beams for each revolution of the x-ray source. The x-ray beam thickness SW, for each of a plurality of x-ray fans equally spaced in z is commonly called the slice width in non-spiral CT terminology. The ratio of the pitch to the slice width in a single ring CT scanner which would give the same axis sampling as would the present multi-ring spiral CT is designated as the effective pitch factor, EPF.

A z-axis sampling spacing $\Delta$ is equal to the pitch divided by 2N, where N is the number of rings. The effective pitch factor EPF is the pitch divided by N multiplied by the slice width, i.e.:

$$PITCH = N \cdot EPF \cdot SW \quad (1)$$

$$\Delta = \frac{PITCH}{2N} = \frac{EPF \times SW}{2} \quad (2)$$

For a dual ring spiral, N=2. A spacing SP between two distinct x-ray fan beams, center-to-center, can be selected from $\Delta$, $3\Delta$, $5\Delta$, ..., i.e.:

$$SP = (2k+1)\Delta \quad (3)$$

for k=0, 1, 2, ..., and $(2k+1) \geq 2/EPF$. The requirement that 2k+1 be greater than or equal to 2 divided by the effective pitch factor forces the physical constraint SP to be greater than or equal to SW. Stated another way, the gap between the x-ray fan is:

$$GAP = SP - SW \quad (4)$$

A gap ratio of the gap to the slice width is:

$$GAP\ RATIO = \frac{GAP}{SW} = (2k+1) \times \frac{EPF}{2} - 1 \quad (5)$$

The value of k is selected based on practical reasons. However, in general, the smallest value of k is preferred because it both permits optimal use of the beginning and end of the spiral data and minimizes the fan skew angle. TABLE 1 illustrates likely choices for N=2 and EPF<2.

TABLE 1

|  | PITCH (mm) | MIN k = 1 GAP (mm) | k = 2 GAP (mm) | k = 3 GAP (mm) |
|---|---|---|---|---|
| N = 2, SW = 4 mm, EPF = 1.333 | 10.667 | 4.000 | 9.333 | 14.67 |
| N = 2, SW = 6 mm, EPF = 1.333 | 16.000 | 6.000 | 14.00 | 22.00 |
| N = 2, SW = 8 mm, EPF = 1.333 | 21.333 | 8.000 | 18.67 | 29.33 |
| N = 2, SW = 4 mm, EPF = 1.250 | 10.000 | 3.500 | 8.500 | 13.50 |
| N = 2, SW = 6 mm, EPF = 1.500 | 18.000 | 7.500 | 16.50 | 25.50 |
| N = 2, SW = 8 mm, EPF = 1.000 | 16.000 | 4.000 | 12.00 | 20.00 |
| N = 2, SW = 10 mm, EPF = 1.167 | 23.333 | 7.500 | 19.17 | 40.83 |

For N=2 and EPF<2, the minimum gap ratio can be defined as:

$$MIN.\ GAP\ RATIO = 0.5 + 1.5 \cdot (EPF - 1) \quad (6)$$

As illustrated in TABLE 2, the effective pitch factor can also be greater than or equal to 2. For EPF$\geq$2, we can also have k=0 and abutting x-ray fans, GAP=0, are acceptable.

TABLE 2

|  | PITCH (mm) | MIN k = 0 GAP (mm) | k = 1 GAP (mm) | k = 2 GAP (mm) |
|---|---|---|---|---|
| N = 2, SW = 4 mm, EPF = 2.00 | 16.000 | 0 | 8 | 16 |

Generalizing to even N>2, TABLE 3 illustrates the above-formulas.

TABLE 3

|  | PITCH (mm) | MIN k = 1 GAP (mm) | k = 2 GAP (mm) | k = 3 GAP (mm) |
|---|---|---|---|---|
| N = 4, SW = 4 mm, EPF = 1.333 | 21.333 | 4.000 | 9.333 | 14.67 |
| N = 4, SW = 6 mm, EPF = 1.333 | 32.000 | 6.000 | 14.00 | 22.00 |
| N = 4, SW = 8 mm, EPF = 1.333 | 42.666 | 8.000 | 18.67 | 29.33 |
| N = 6, SW = 4 mm, EPF = 1.250 | 30.000 | 3.500 | 8.500 | 13.50 |
| N = 6, SW = 6 mm, EPF = 1.500 | 54.000 | 7.500 | 16.50 | 25.50 |
| N = 6, SW = 8 mm, EPF = 1.000 | 48.000 | 4.000 | 12.00 | 20.00 |
| N = 8, SW = 10 mm, | 93.333 | 7.500 | 19.17 | 40.83 |

TABLE 3-continued

| | PITCH (mm) | MIN k = 1 GAP (mm) | k = 2 GAP (mm) | k = 3 GAP (mm) |
|---|---|---|---|---|
| EPF = 1.167 | | | | |

TABLE 4 continues the illustration for a zero gap and the effective pitch factor equal to 2. For EPF≧2, we can also have k=0:

TABLE 4

| | PITCH (mm) | MIN k = 0 GAP (mm) | k = 1 GAP (mm) | k = 2 GAP (mm) |
|---|---|---|---|---|
| N = 8, SW = 4 mm, EPF = 2.00 | 64.000 | 0 | 8 | 16 | and abutting x-ray fans (GAP=0) are acceptable for even N only for EPF≧2.

For the N odd case, N≧3, we still have PITCH=N·EPF·SW and $\Delta$=EPF·SW/2, but now SP=k·$\Delta$ {k=1,2, ...; k≧2/EPF; k≠jN(j=1,2, ...)}. The second k condition again enforces the physical constraint SP≧SW. The third k condition is unique to the odd N case and is needed to ensure full use of ray direction redundancy to improve z-axis sampling.

TABLE 5 illustrates several examples for N odd and the effective pitch factor greater than or equal to 1 and less than 2.

TABLE 5

| | PITCH (mm) | MIN k = 2 GAP (mm) | k = 4 GAP (mm) | k = 5 GAP (mm) |
|---|---|---|---|---|
| N = 3, SW = 4 mm, EPF = 1.333 | 16.000 | 1.333 | 6.667 | 9.333 |
| N = 3, SW = 6 mm, EPF = 1.333 | 24.000 | 2.000 | 10.00 | 14.00 |
| N = 3, SW = 8 mm, EPF = 1.000 | 24.000 | 0.000 | 8.000 | 12.00 |

| | PITCH (mm) | k = 2 GAP (mm) | k = 3 GAP (mm) | k = 4 GAP (mm) |
|---|---|---|---|---|
| N = 5, SW = 4 mm, EPF = 1.250 | 25.000 | 1.000 | 3.500 | 6.000 |
| N = 5, SW = 6 mm, EPF = 1.500 | 45.000 | 3.000 | 7.500 | 12.00 |
| N = 5, SW = 8 mm, EPF = 1.000 | 40.000 | 0.000 | 4.000 | 8.000 |
| N = 7, SW = 10 mm, EPF = 1.167 | 81.667 | 1.667 | 7.500 | 13.33 |

Generally, we see that PITCH=N·EPF·SW. We have made the above choices of N, SW, and EPF to illustrate that for odd N, unlike the even N case, abutting x-ray fans (GAP=0) are always possible for EPF=1.00. Thus, the gaps are the same as for N=2.

In this situation, the spacing SP is defined as:

$$SP = k \cdot \Delta \quad (7)$$

for k=1, 2, ..., k≧2/EPF, k≠jN, (j=1, 2, ...). These conditions on k again enforce the physical constraint that the spacing is greater than or equal to the slice width. The requirement that k not equal jN is unique to the odd case and is used to ensure full use of the ray direction redundancy to improve z-axis sampling.

Now, the minimum gap ratio is not as simply summarized as in the N even case. TABLE 6 illustrates examples for N odd and the effective pitch factor equal to 2.

For EPF≧2, we can also have k=1:

TABLE 6

| | PITCH (mm) | MIN k = 1 GAP (mm) | k = 2 GAP (mm) | k = 3 GAP (mm) |
|---|---|---|---|---|
| N = 5, SW = 4 mm, EPF = 2.00 | 40.000 | 0 | 4 | 8 |

Figure 9:
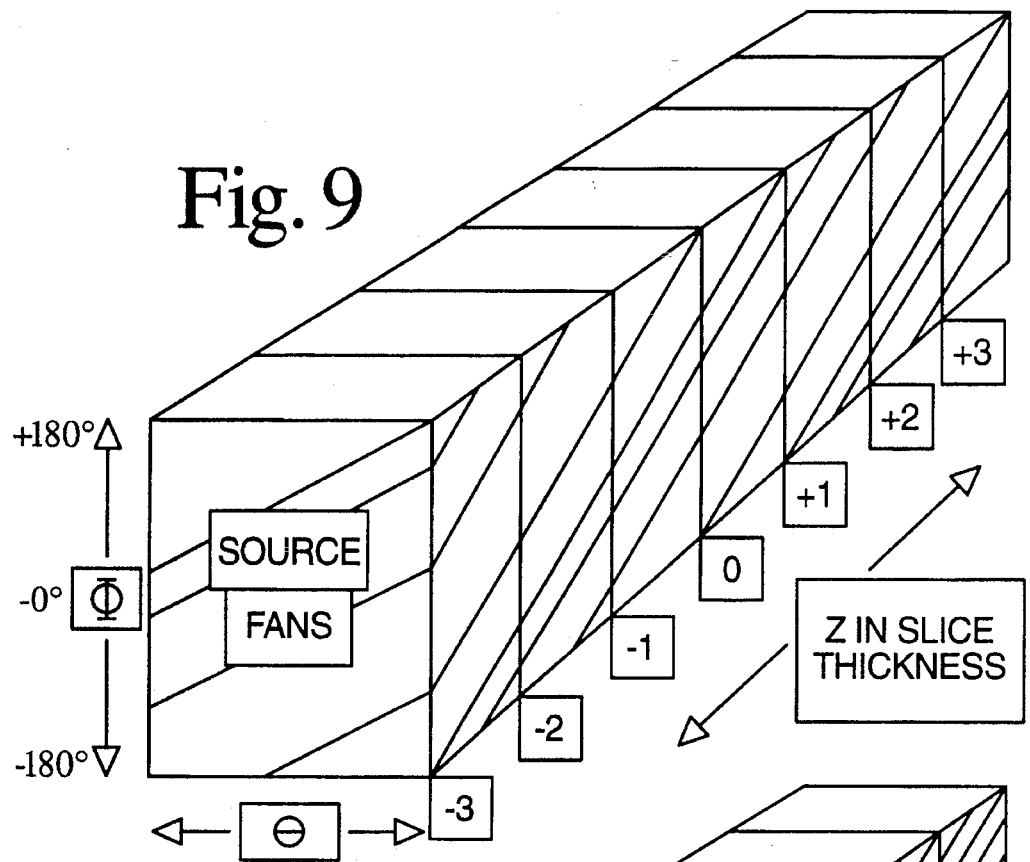
FIG. 9 illustrates the spiral trajectory with a pitch factor equal to 4 and four rings with a half gap effective detector spacing; and, FIG. 10 illustrates the spiral trajectory with a pitch factor equal to 4 and four rings with half gaps, but with the ray redundancy removed.
Figure 10:
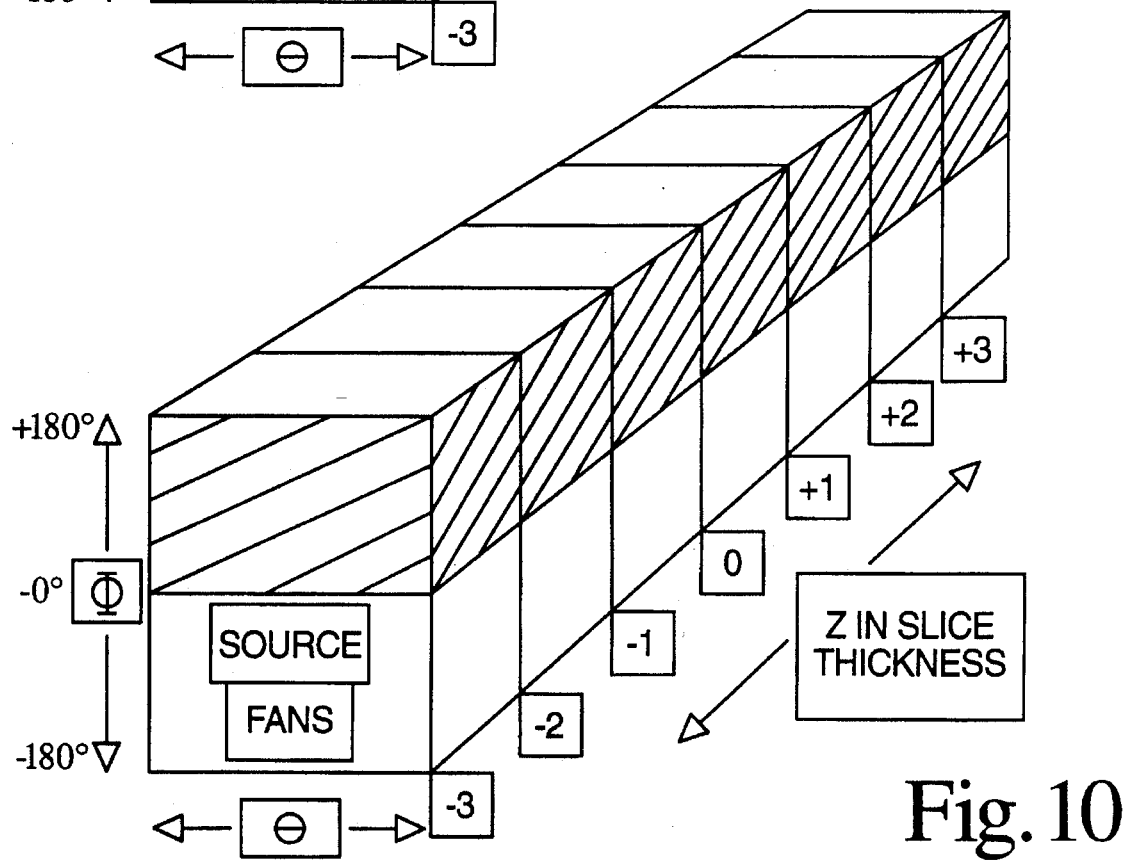

With reference to FIG. 9, when there are four slices, i.e. N=4, a pitch factor of 4 can be used with half gaps. With the ray redundancy removed in FIG. 10, two samples are obtained per slice width.

A step or means 104 selects the effective pitch factor. A step or means 106 responds to operator selection of the desired coverage, i.e. the length of the imaged volume along the z-axis to provide a corresponding electronic selection signal. A step or means 108 computes the optimal x-ray beam gap in accordance with the above-equations or tables for the selected scan parameters from the electronic selection signals. The computing means or step 108 sets the system position, the collimator position, and the speed of the motor 32. The z-axis slice positions are selected or designated in a step or means 110. More specifically to the preferred embodiment, the number of equally-spaced slices within the selected volume is designated or conversely, the thickness or resolution between adjacent image slices. The step or means 112 combines data from several rings to reconstruct images at the desired slice positions using data from nearest adjacent corresponding rays to either side of the slice.

For two detector rings, one of the two spirals lags the other by 90°. The data from each detector ring are weighted by a function with half the width of a normal weighted function of a single ring. These data are then combined together in order to reconstruct a cross-section.

For three detector rings, the spirals are 60° offset such that the three data sets abut and have their central ray on the plane of the slice. Generalizing to N rings of detectors, the spirals are 180°/N offset such that the data sets abut and are centered on the plane of the slice.

The invention has been described with reference to the preferred embodiment. Obviously, modifications and alterations will occur to others upon reading and understanding the preceding detailed description. It is intended that the invention be construed as including all such modifications and alterations insofar as they come within the scope of the appended claims or the equivalents thereof.

Having thus described the preferred embodiment, the invention is now claimed to be:

1. A spiral CT scanner comprising:

an x-ray source for irradiating an examination region with penetrating radiation;

a means for rotating the x-ray source around the examination region;

a subject support for moving a subject through the examination region concurrently with rotation of the radiation source around the examination region;

a plurality of radiation detectors positioned adjacent the examination region along a plurality of parallel arcs for receiving radiation from the radiation source which has traversed the subject;

a collimator for dividing radiation from the x-ray source into at least two parallel fan-beams such that x-rays traverse the subject along at least two generally parallel fan-shaped beams between the source and the detectors, which x-ray fan-beams spiral concurrently around the subject in a longitudinally offset relationship;

a means for adjusting an effective spacing and thickness of the x-ray fan-beams; and a means for reconstructing output data from the detectors into a volume image representation.

2. The spiral CT scanner as set forth in claim 1 wherein the adjusting means includes an adjustable septum, adjusting the septum adjusts both a gap between the fan beams and a thickness of each beam.

3. The spiral CT scanner as set forth in claim 2 wherein the collimator further includes adjustable outer collimator members for further selectively adjusting the thickness of the fan beams.

4. The spiral CT scanner as set forth in claim 3 further including a collimator control means for controlling the septum and collimator members for coordinately setting the gap between the fan beams and the fan beam thickness.

5. The spiral CT scanner as set forth in claim 4 further including a look-up table connected with the collimator control means for storing gap and fan beam thickness characteristics corresponding to each of a plurality of preselected diagnostic examinations.

6. The spiral CT scanner as set forth in claim 5 further including an operator control console for designating one of the preselected diagnostic examinations, the control console being connected with the look-up table and collimator control means such that the septum and collimator members are positioned to define the gap and fan beam thickness corresponding to the selected diagnostic examination.

7. The spiral CT scanner as set forth in claim 2 further including:

a sampling means for sampling radiation attenuation data from the radiation detectors;

a view processor means for combining sampled radiation data from the at least two parallel x-ray fans into common data sets;

a reconstruction means for reconstructing the common data sets into a plurality of parallel slice image representations.

8. A spiral CT scanner comprising:

a subject support;

an x-ray source mounted for rotation around the subject support;

a plurality of radiation detectors for receiving radiation from the radiation source which has traversed the subject, the radiation detectors being positioned in a plurality of lines which lines each extend in an arc-like fashion;

a means for coordinating rotational movement of the x-ray source and relative longitudinal movement between the subject support and the x-ray source and detectors, such that x-rays traverse the subject along at least two generally parallel fan-shaped paths between the source and the detectors, which x-ray fans spiral concurrently around the subject in a longitudinally offset relationship;

a means for adjusting an effective spacing and width of the x-ray fans;

a means for selection of slice thickness, an effective pitch factor, and a longitudinal extent of a volume to be imaged; and, a means for determining the effective spacing and width of the x-ray fans in accordance with the selected slice thickness and pitch factor.

9. The spiral CT scanner as set forth in claim 8 wherein the effective spacing and width determining means includes a plurality of look-up tables.

10. A method of using a spiral CT scanner which includes a subject support, an x-ray source, a means for rotating the x-ray source around the patient support, a plurality of radiation detectors arranged along a plurality of parallel arcs for receiving radiation from the radiation source which has traversed the subject, and a means for coordinating rotational movement of the x-ray source and relative longitudinal movement between the subject support and the x-ray source and detector arcs along a longitudinal axis, such that x-rays traverse the subject along at least two generally parallel fan-shaped paths between the source and the detector arcs, which x-ray fans spiral concurrently around the subject in a longitudinally offset relationship, THE METHOD COMPRISING:

selectively adjusting a spacing between x-ray fans to optimize resolution;

after the spacing between fans has been adjusted, rotating the fans concurrently around the subject support and collecting radiation attenuation data with the detector arcs;

reconstructing the attenuation data into a volume image representation.

11. The method as set forth in claim 10, further including:

selecting a width of the x-ray fans.

12. The method as set forth in claim 11 wherein the CT scanner further includes a means for selection of an image slice thickness, an effective pitch factor, and a longitudinal extent of a volume to be imaged, the method further comprising:

determining the spacing between x-ray fans from the slice thickness and selected effective pitch factor which optimizes resolution.

13. The method as set forth in claim 12 wherein the determining step includes retrieving the spacing from a look-up table.

14. The method as set forth in claim 10 in which there are two x-ray fans, each of which has a leading edge and a trailing edge, the method further including:

adjusting the spacing between the two x-ray fans such that the leading edge of both fans intersect a common plane transverse to the longitudinal axis at 90° offset angular orientations around the longitudinal axis.

15. The method as set forth in claim 14 wherein the reconstructing step includes reconstructing a plurality of parallel slice image representations and further including:

prior to the reconstructing step, combining attenuation data from selected portions of weighted attenuation data from the two x-ray fans such that attenuation data from both fans contribute to a common slice image representation.

16. The method as set forth in claim 14 wherein the reconstructing step includes reconstructing a plurality of parallel slice image representations and further including:

reconstructing portions of the attenuation data from the two x-ray fans into images and combining the images into the image representation.

17. The method as set forth in claim 10 in which there are N x-ray fans, where N is a positive integer greater than 2, each of the x-ray fans having a leading edge and a trailing edge, the method further including:

adjusting the spacing between x-ray fans such that a leading edge of each fan intersects a common plane transverse to the longitudinal axis at 180°/N offset angular orientations relative to each other around the longitudinal axis.

18. The method as set forth in claim 17 wherein the reconstructing step includes reconstructing a plurality of parallel slice image representations and further including:

prior to the reconstructing step, combining attenuation data from each of the N x-ray fans for reconstruction into a common slice image representation.

19. The method as set forth in claim 17 wherein the reconstructing step includes reconstructing a plurality of parallel slice image representations and further including:

reconstructing attenuation data from each of the N x-ray fans and combining the reconstructed data into a common slice image representation.

20. In a method of spiral CT scanning in which N x-ray fan-beams rotate in concentric spirals around a longitudinal axis, where N is an integer greater than 1, the improvement comprising:

adjusting a center-to-center spacing between the x-ray fan beams such that a leading edge ray of each x-ray fan-beam intersects a common plane transverse to the longitudinal axes 180°/N offset from each other.

21. In the method as set forth in claim 20, the improvement further comprising:

adjusting a width of the x-ray fan beams.

22. The method as set forth in claim 20 further including:

collecting attenuation data fans from each of the fan-beams at each of a multiplicity of locations along a plurality of spirals;

combining the attenuation data fans from a plurality of the locations;

reconstructing the combined attenuation data fans into a plurality of parallel slice images such that many attenuation data fans contribute to each slice image representation.

23. The method as set forth in claim 20 in further including:

reconstructing attenuation data from multiple fan beam locations into a plurality of reconstruction data sets and combining the reconstructed data sets such that many fan beams contribute to each of a plurality of parallel slice image representations.

24. A spiral CT scanner comprising:

an x-ray source for irradiating an examination region with penetrating radiation, the x-ray source being mounted for rotation around the examination region;

a subject support for moving a subject through the examination region concurrently with rotation of the radiation source around the examination region;

a plurality of arcs along which radiation detectors are disposed for receiving radiation from the radiation source which has traversed the subject;

a collimator for dividing radiation from the x-ray source into at least two parallel fan-beams, the collimator comprising:

a septum for adjusting a spacing between at least two parallel fan-beams of radiation from a source of radiation;

collimator members, the collimator members interacting with the septum to adjust a thickness of each fan-beam;

a look-up table for storing a plurality of septum and collimator member positions corresponding to each of a plurality of preselectable examination procedures;

a collimator control connected with the look-up table, the septum, and the collimator members for automatically positioning the septum and collimator members in accordance with a selected one of the preselectable examination procedures; and, a reconstruction processor for reconstructing output data from the detectors into a volume image representation.

* * * * *